United States Patent [19]

Kumazawa et al.

[11] Patent Number: 4,547,496

[45] Date of Patent: Oct. 15, 1985

[54] ANTIULCER [1] BENZEPINO[3,4-b]PYRIDINE AND COMPOSITIONS

[75] Inventors: Toshiaki Kumazawa; Yoshimasa Oiji; Hiroshi Tanaka; Katsuichi Shuto, all of Shizuoka, Japan

[73] Assignee: Kyowa Hakko Kogyo Co., Ltd., Tokyo, Japan

[21] Appl. No.: 623,084

[22] Filed: Jun. 21, 1984

[30] Foreign Application Priority Data

Jun. 24, 1983 [JP] Japan .................. 58-113831
Oct. 5, 1983 [JP] Japan .................. 58-186129
Oct. 21, 1983 [JP] Japan .................. 58-196976

[51] Int. Cl.$^4$ .................. A61K 31/44; A61K 31/535; C07D 491/044; C07D 495/04
[52] U.S. Cl. .................. 514/218; 514/231; 514/234; 514/237; 514/252; 514/291; 260/244.4; 544/126; 544/361; 546/80; 546/89
[58] Field of Search .................. 544/126, 361; 546/80, 546/89; 424/248.51, 248.54, 248.56, 250, 256, 258, 263, 267; 260/244.4

[56] References Cited

PUBLICATIONS

Ueno et al., Chemical Abstracts, vol. 83 (1975) No. 28301m.

Primary Examiner—Robert W. Ramsuer
Attorney, Agent, or Firm—Antonelli, Terry & Wands

[57] ABSTRACT

A novel [1] benzepino[3,4-b]pyridine derivative having antiulcer activity is represented by the formula (I):

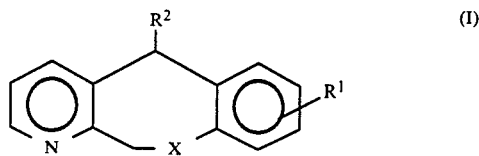

wherein $R^1$ represents a hydrogen atom, an alkyl group, a halogenated alkyl group, an alkoxy group or a halogen atom; $R^2$ represents

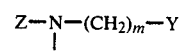

wherein Y represents an amino group, a substituted amino group, a heterocyclic group or a substituted heterocyclic group; Z represents a hydrogen atom, an alkyl group or an acyl group; and m is an integer of 1-3,

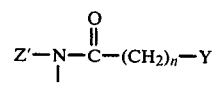

wherein Z' represents a hydrogen atom or an alkyl group; Y has the same meaning as defined above, and n is 0, 1 or 2; or

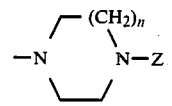

wherein Z and n have the same meanings as defined above; X represents an oxygen atom or a sulfur atom. Also disclosed are pharmaceutically acceptable acid addition salts of the compound represented by the formula (I).

26 Claims, No Drawings

ANTIULCER [1] BENZEPINO[3,4-b]PYRIDINE AND COMPOSITIONS

The present invention relates to a novel [1]benzepino[3,4-b]pyridine derivative, the pharmaceutically acceptable acid addition salts thereof and a pharmaceutical composition containing, as the active ingredient, a novel [1]benzepino[3,4-b]pyridine derivative.

More particularly, the present invention pertains to a novel [1]benzepino[3,4-b]pyridine derivative represented by the formula (I):

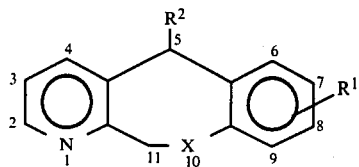

wherein $R^1$ represents a hydrogen atom, an alkyl group, a halogenated alkyl group, an alkoxy group or a halogen atom; $R^2$ represents

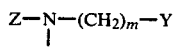

wherein Y represents an amino group, a substituted amino group, a heterocyclic group or a substituted heterocyclic group; Z represents a hydrogen atom, an alkyl group or an acyl group; and m is an integer of 1-3,

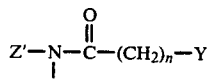

wherein Z' represents a hydrogen atom or an alkyl group; Y has the same meaning as defined above, and n is 0, 1 or 2; or

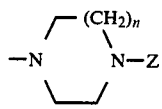

wherein Z and n have the same meanings as defined above; X represents an oxygen atom or a sulfur atom; and the pharmaceutically acceptable acid addition salts thereof.

In addition, the present invention pertains to a pharmaceutical composition comprising a pharmaceutical carrier and, as an active ingredient, an effective amount of a novel [1]benzepino[3,4-b]pyridine derivative represented by the formula (I).

The present compound has antiulcer activity and is therefore useful as antiulcer agent. In the formula (I), the alkyl group for $R^1$, Z and Z' include an alkyl group having 1-5 carbon atoms, such as a methyl group, an ethyl group, a propyl group, a butyl group and a pentyl group; the halogenated alkyl group for $R^1$ includes a halogenated alkyl group having 1-3 carbon atoms, such as a trifluoromethyl group, a trichloromethyl group and a tribromomethyl group; the alkoxy group for $R^1$ includes an alkoxy group having 1-5 carbon atoms, such as a methoxy group, an ethoxy group, a propoxy group, a butoxy group and a pentyloxy group; the halogen atom for $R^1$ includes a fluorine atom, a chlorine atom, a bromine atom and an iodine atom; the acyl group for Z includes an acyl group having 1-5 carbon atoms, such as a formyl group, an acetyl group, a propionyl group, a butyryl group, a valeryl group, a fluoroacetyl group, a difluoroacetyl group, a trifluoroacetyl group, a chloroacetyl group, a dichloroacetyl group, a trichloroacetyl group, a bromoacetyl group, a dibromoacetyl group and a tribromoacetyl group; the heterocyclic group for Y includes a piperazine group, a piperidine group, a morpholine group, a pyrrolidine group, a pyridine group, a quinuclidine group, a imidazole group, a indole group, a quinoline group and a pyrrolitizine group; a substituent for the substituted heterocyclic group includes an alkyl group having 1-5 carbon atoms such as a methyl group, an ethyl group, a propyl group, a butyl group and a pentyl group or an halogen atom such as a fluorine atom, a chlorine atom, a bromine atom and an iodine atom; a substituent for the substituted amino group includes mono or di-substituted amino group, for example, an alkyl group having 1-5 carbon atoms, such as a methyl group, an ethyl group, a propyl group, a butyl group and a pentyl group.

The pharmaceutically acceptable acid addition salts of the present compound are inorganic acid salts such as hydrochlorides, hydrobromides, phosphates, sulfates, etc. and organic acid salts such as acetates, maleate, fumarates, tartrates, citrates, oxalates and benzoates.

The present compound is prepared from compound II represented by the formula (II):

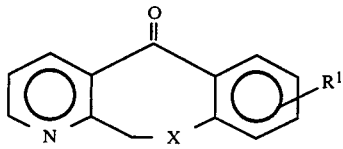

wherein $R^1$ and X have the same meanings as defined above, by utilizing well-known organic synthetic methods as described below.

Methods for preparation of some of the compound II are known and have been disclosed, for example, in Japanese Published Unexamined Patent Application No. 117496/1974 and Chem. Pharm. Bull., 29, 3515 (1981). The others whose preparation has not been disclosed can also be obtained in similar manner.

Representative processes for production of the present compound A through J, are explained below:

Process A

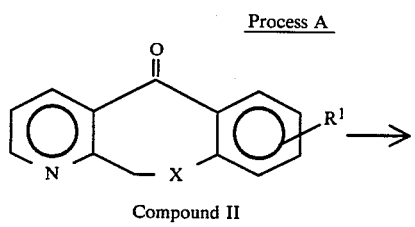

Compound II

-continued
Process A

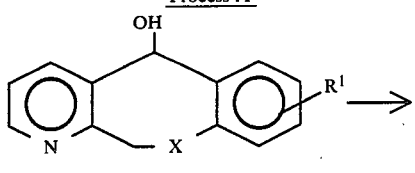

Compound III

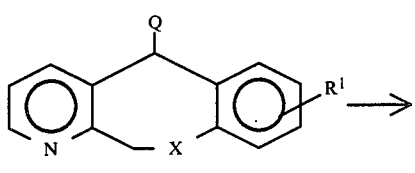

Compound IV

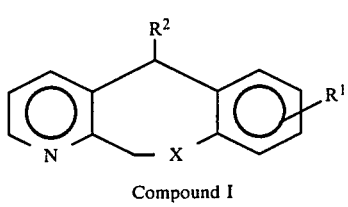

Compound I wherein $R^1$, $R^2$ and X have the same meanings as defined above; and Q represents a halogen atom. Compound II is reduced into compound III, which is reacted with a halogenating agent to give compound IV or acid addition salt thereof. It is then reacted with an amine [Z''—NH—$(CH_2)_m$—Y (compound V) or

(compound VI)

wherein Y, Z, m and n have the same meanings as defined above; and Z'' represents a hydrogen atom or an alkyl group having 1 to 5 carbon atoms] to obtain compound I.

Process A is described in more detail below.

Compound III is prepared by reducing compound II usually with a metal hydride complex, such as lithium aluminum hydride and sodium borohydride.

In the case of using lithium aluminum hydride as a reducing agent, compound II is dissolved or suspended in an anhydrous solvent such as diethyl ether, diisopropyl ether, tetrahydrofuran and ethylene glycol dimethyl ether. Then, 0.3 to 2.0 equivalent, based on compound II, of lithium aluminum hydride is added thereto, and the mixture is stirred at an appropriate temperature from 0° C. to the boiling point of the solvent used for 30 minutes to 3 hours to complete the reduction. Compound III is obtained by usual workup of the reaction mixture.

In the case of using sodium borohydride, compound II is dissolved or suspended in a solvent such as water, methanol, ethanol, isopropanol, ethylene glycol dimethyl ether, dimethylformamide and dimethylsulfoxide. Then, 0.3 to 1.0 equivalent, based on compound II, of sodium borohydride is added thereto, and the mixture is stirred at an appropriate temperature from 0° to 60° C. for one to 8 hours to complete the reduction. Compound III is obtained by usual workup of the reaction mixture.

It is also possible to use catalytic hydrogenation for the reduction of compound II into compound III.

Compound III thus obtained is easily converted to compound IV or acid addition salt thereof by reaction with a halogenating agent such as thionyl halides and phosphorus halides. As a thionyl halide, thionyl chloride or thionyl bromide is used. Compound III is reacted with excess thionyl halide, in the presence or absence of a solvent such as benzene, toluene, xylene, dichloromethane, chloroform, carbon tetrachloride, dimethylformamide and diethyl ether, at an appropriate temperature from 0° to 70° C. for one to 5 hours in the presence of a tertiary amine, if necessary, such as pyridine, quinoline, dimethylaniline, triethylamine and diisopropylethylamine, to give compound IV or acid addition salt thereof. The typical examples of phosphorus halides include phosphorus trichloride, phosphorus pentachloride, phosphorus tribromide, phosphorus pentabromide, phosphorus oxychloride and phosphorus oxybromide. These compounds may be reacted with compound III under similar conditions as in the case of thiony halides, affording compound IV or acid addition salt thereof.

Alternatively, hydrogen halides are used for halogenation of compound III to form compound IV or acid addition salt thereof.

Compound I is prepared by reaction of compound IV or acid addition salt thereof with compound V or compound VI. The reaction is carried out at an appropriate temperature from −10° to 120° C. for 30 minutes to 3 hours using 2 to 10 equivalent of compound V or VI, based on compound IV or acid addition salt thereof, and using an inert solvent, if necessary, such as dichloromethane, chloroform, carbon tetrachloride, benzene, toluene, xylene, diethyl ether, diisopropyl ether, tetrahydrofuran, dioxane, hexane, cyclohexane, acetonitrile, carbon disulfide, ethyl acetate and dimethylformamide.

It is possible to reduce the amount of compound V or VI used to one equivalent, if a base such as sodium carbonate, sodium bicarbonate, potassium carbonate, potassium bicarbonate, pyridine, quinoline, dimethylaniline, triethylamine and diisopropylethylamine, is employed as a trapper of hydrogen halide:

Process B

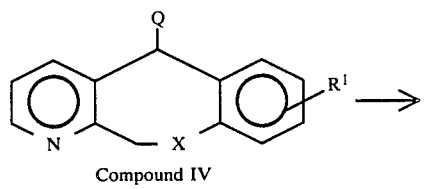

Compound IV

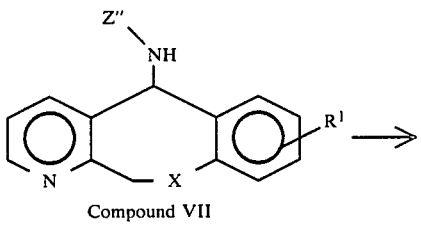

Compound VII

-continued
Process B

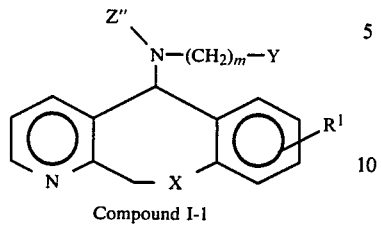

Compound I-1 wherein X, Y, Z'', Q and m have the same meanings as defined above.

Compound IV or acid addition salt thereof, obtained in Process A, is subjected to reaction with ammonia or an amine [Z''—NH₂ (compound VIII), wherein Z'' has the same meaning as defined above)] to form compound VII, which is then reacted with compound IX of formula Y—(CH₂)$_m$—W wherein Y and m have the same meanings as defined above; and W represents a halogen atom such as chlorine atom, bromine atom and iodine atom or a sulfonyloxy group such as methylsulfonyloxy group, phenylsulfonyloxy group and p-toluenesulfonyloxy group, or acid addition salt thereof, to give compound I-1 of this invention.

Process B is explained in more detail below.

Compound VII is prepared by reaction of compound IV or acid addition salt thereof with an excess amount of compound VIII in the presence or absence of an inert solvent such as benzene, toluene, xylene, dichloromethane, chloroform, carbon tetrachloride, dimethylformamide, diethyl ether, tetrahydrofuran, dioxane, acetonitrile and ethyl acetate, at an appropriate temperature from −78° to 50° C. for 30 minutes to 3 hours.

Compound VII thus obtained is then reacted with 1 to 5 equivalents of compound IX or acid addition salt thereof at an appropriate temperature from 0° to 120° C. for 30 minutes to 6 hours in a solvent such as dichloromethane, chloroform, carbon tetrachloride, benzene, toluene, xylene, diethyl ether, diisopropyl ether, tetrahydrofuran, dioxane, hexane, cyclohexane, methanol, ethanol, propanol, acetonitrile, carbon disulfide, ethyl acetate and dimethylformamide in the presence of a base, if necessary, such as sodium carbonate, sodium bicarbonate, potassium carbonate, potassium bicarbonate, pyridine, quinoline, dimethylaniline, triethylamine and diisopropylethylamine, and in the presence of a catalytic amount of an iodide, if necessary, such as sodium iodide and potassium iodide, to give compound I-1:

Process C

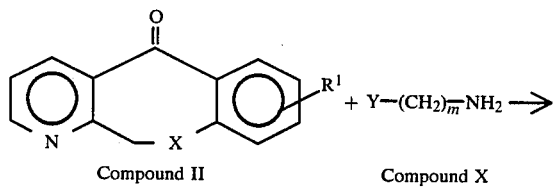

Compound II         Compound X

-continued
Process C

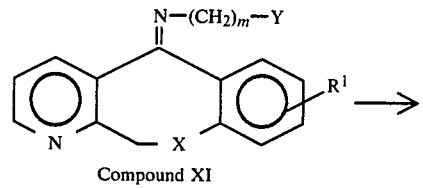

Compound XI

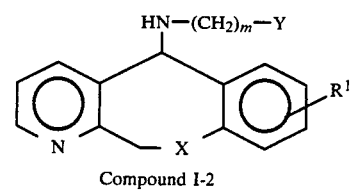

Compound I-2 wherein R¹, X, Y and m have the same meanings as defined above.

Compound I-2 of this invention is prepared by condensation of compound II with compound X to afford compound XI, followed by reduction.

For example, compound II is subjected to reaction with 5 to 10 equivalents based on compound II, of compound X in a solvent such as dichloromethane, chloroform, carbon tetrachloride, benzene, toluene, xylene, carbon disulfide and dimethylformamide, at an appropriate temperature from 0° to 120° C. for 6 to 48 hours in the presence of 0.5 to 1.0 equivalent, based on compound II of a Lewis acid such as titanium tetrachlorides and tin tetrachlorides, to give compound XI. This product is then reduced by using a method commonly employed for reduction of imines to amines, for example, reduction with a metal hydride complex such as lithium aluminum hydride, sodium borohydride and sodium borocyanohydride, or by catalytic hydrogenation, whereby compound I-2 is obtained:

Process D

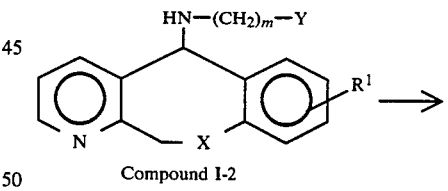

Compound I-2

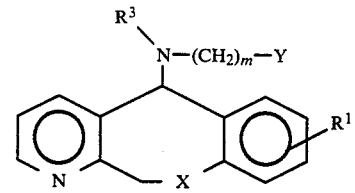

Compound I-3 wherein R¹, X, Y and m have the same meanings as defined above; and R³ represents an acyl group having 1 to 5 carbon atoms.

Examples of the acyl group having 1 to 5 carbon atoms for R³ include formyl, acetyl, propionyl, butyryl, valeryl, fluoroacetyl, difluoroacetyl, trifluoroacetyl, chloroacetyl, dichloroacetyl, trichloroacetyl, bromoacetyl, dibromoacetyl, tribromoacetyl groups, etc.

Compound I-3 of this invention is prepared by acylating compound I-2, obtained by Processes A through C, by a method usually used for acylation of amino groups, for example, by using carbonyl halides, carboxylic anhydrides or active esters:

Process E

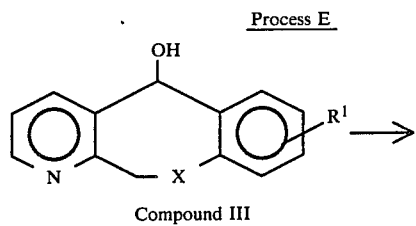

Compound III

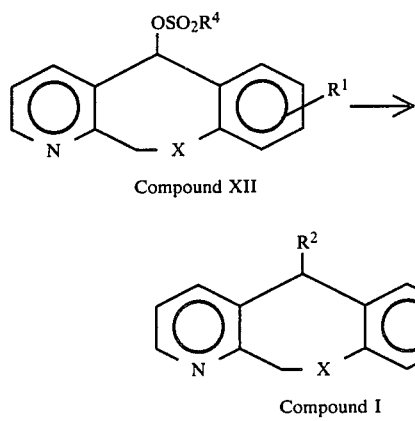

Compound XII

Compound I wherein $R^1$, $R^2$ and X have the same meanings as defined above; and $R^4$ represents an alkyl group, a phenyl group or a substituted phenyl group.

Examples of the substituted phenyl group includes p-tolyl group. Compound I of this invention is prepared by reaction of compound III, obtained in Process A, with a sulfonylating agent to afford compound XII or acid addition salt thereof, followed by reaction with an amine (compound V or VI):

Process F

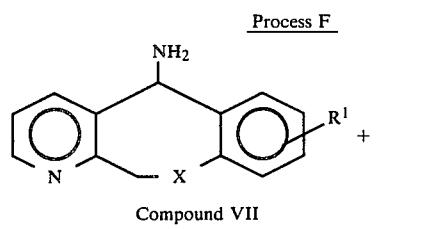

Compound VII

Y—(CH$_2$)$_{m-1}$—CHO ⟶

Compound XIII

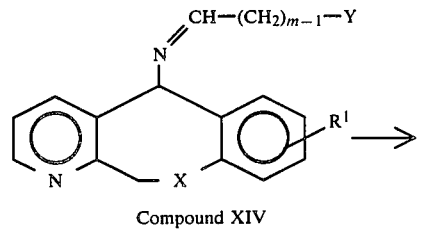

Compound XIV

-continued
Process F

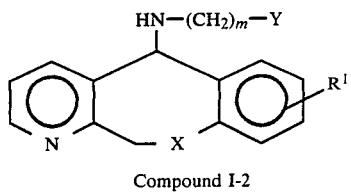

Compound I-2 wherein $R^1$, X, Y and m have the same meanings as defined above. Compound I-2 is prepared by condensation of compound VII', compound VII (wherein Z is a hydrogen atom) obtained in Process B, with compound XIII to afford compound XIV, followed by reduction:

Process G

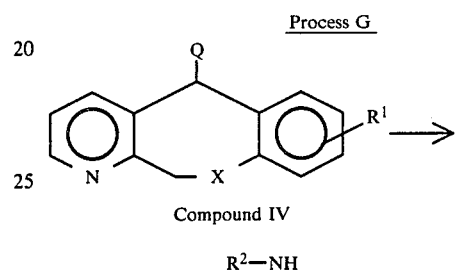

Compound IV

Compound XV

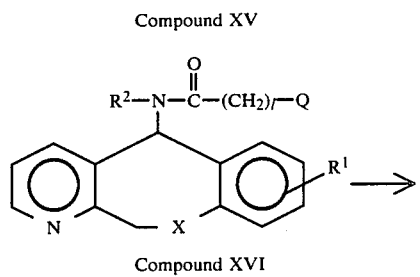

Compound XVI

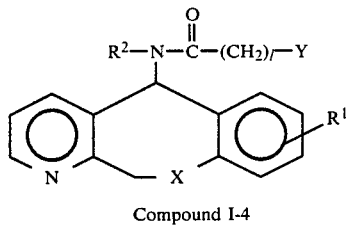

Compound I-4 wherein $R^1$, $R^2$, X, Y and Q have same meanings as defined above; and l is 1 or 2.

Compound IV or acid addition salt thereof, obtained in Process A, is reacted with ammonia or an amine [$R^2$—NH$_2$ (compound XVII), wherein $R^2$ has the same meaning as defined above] to form compound XV, followed by reaction with a halogenated acyl halide [Q—CO(CH$_2$)$_l$—Q (compound XVIII), wherein Q and l have the same meanings as defined above)] or with a halogenated acid anhydride {[Q—(CH$_2$)$_l$—CO]$_2$O (compound XIX), wherein Q and l have the same meanings as defined above)} to give compound XVI or acid addition salt thereof. Compound I-4 of this invention is prepared by reaction of compound XVI or acid addition salt thereof thus obtained with compound XX (Y—H, wherein Y has the same meaning as defined above).

Process G is described in more detail below.

Compound IV or acid addition salt thereof is subjected to reaction with excess ammonia or a compound XVII, in the presence or absence of an inert solvent, such as benzene, toluene, xylene, dichloromethane, chloroform, carbon tetrachloride, dimethylformamide, diethyl ether, tetrahydrofuran, dioxane, acetonitrile and ethyl acetate, at an appropriate temperature from −78° to 50° C. for 30 minutes to 3 hours, whereby compound XV is obtained.

Then, compound XV is reacted with 1 to 1.5 equivalents of compound XVIII in an inert solvent such as benzene, toluene, xylene, dichloromethane, chloroform, carbon tetrachloride, dimethylformamide, diethyl ether, tetrahydrofuran and dioxane in the presence of a base, if necessary, such as pyridine, triethylamine and diisopropylethylamine, at an appropriate temperature from −20° to 50° C. for 30 minutes to 2 hours, whereby compound XVI or acid addition salt thereof is obtained. Alternatively, compound VI is prepared by adding 1 to 2 equivalents of compound XVIII to a mixture of compound XV, an organic solvent such as benzene, toluene, xylene and diethyl ether, and an aqueous solution of a base such as sodium hydroxide, potassium hydroxide, sodium carbonate and potassium carbonate, at an appropriate temperature from −20° to 50° C.

It is also possible to prepare compound XVI by reaction of compound XV with compound XIX.

Compound I-4 is prepared by reaction of compound XVI or acid addition salt thereof with compound XX. The reaction is carried out at an appropriate temperature from room temperature to 120° C. for 2 to 8 hours, using 2 to 5 equivalents of compound XX, based on compound XVI or acid addition salt thereof, and using an inert solvent, if necessary, such as benzene, toluene, xylene, dichloromethane, chloroform, carbon tetrachloride, dimethylformamide, diethyl ether, tetrahydrofuran, dioxane, acetonitrile, hexane and ethyl acetate, in the presence of an iodide, if necessary, such as potassium and sodium iodides. It is also possible to reduce the amount of compound XX used to one equivalent, if a base, such as sodium carbonate, sodium bicarbonate, potassium carbonate, potassium bicarbonate, triethylamine and diisopropylethylamine, is employed as a trapper of hydrogen halide:

Process H

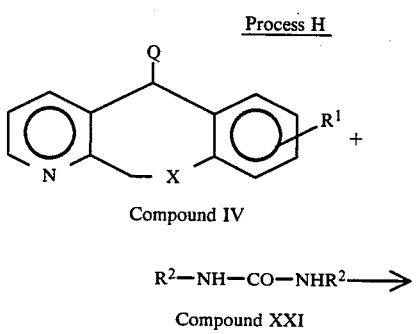

Compound IV

R²—NH—CO—NHR² ⟶

Compound XXI

-continued
Process H

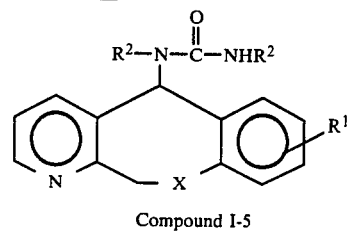

Compound I-5 wherein R¹, R², X and Q have the same meanings as defined above.

Compound I-5 of this invention is prepared by reaction of compound IV or acid addition salt thereof, obtained in Process A, with compound XXI.

This process is explained in more detail below.

Compound IV or acid addition salt thereof is subjected to reaction with 1 to 3 equivalents of compound XXI in the presence of a base such as sodium carbonate, sodium bicarbonate, potassium carbonate, potassium bicarbonate, pyridine, dimethylamine, triethylamine and diisopropylamine, using an inert solvent, if necessary, such as dichloromethane, chloroform, carbon tetrachloride, benzene, tolulene, xylene, diethyl ether, diisopropyl ether, tetrahydrofuran, dioxane, hexane, acetonitrile, dimethylformamide and ethyl acetate, at an appropriate temperature from −10° to 100° C. for 30 minutes to 3 hours, whereby compound I-5 is obtained:

Process I

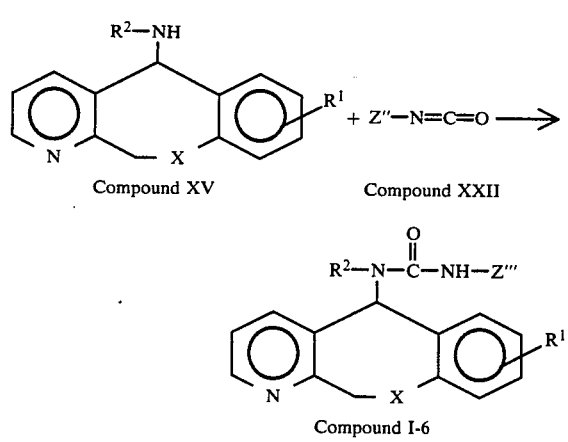

Compound XV Compound XXII

Compound I-6 wherein R¹, R², Z″ and X have the same meanings as defined above; and Z‴ represents an alkyl group having 1 to 5 carbon atoms.

Compound I-6 of this invention is prepared by reaction of compound XV with compound XXII:

Process J

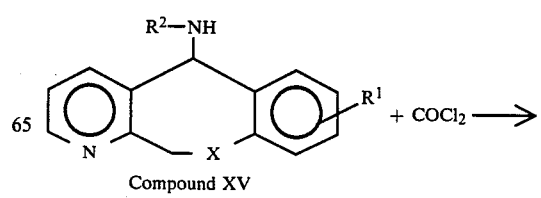

Compound XV

-continued
Process J

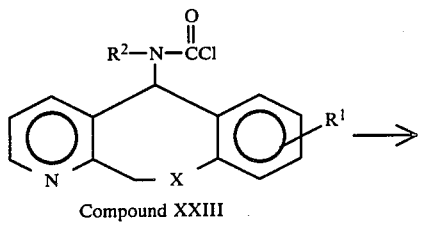

Compound XXIII

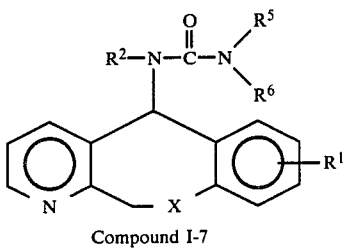

Compound I-7 wherein $R^1$, $R^2$ and X have the same meanings as defined above; and $R^5$ and $R^6$ represent hydrogen atom or an alkyl group having 1 to 5 carbon atoms.

Reaction of compound XV, obtained in Process G, with phosgen gives compound XXIII, which is then subjected to reaction with an amine [HNR$^5$R$^6$ (compound XXIV), wherein $R^5$ and $R^6$ have the same meanings as defined above], whereby compound I-7 of this invention is obtained.

Compounds of this invention prepared by Processes A through J described above are obtained as free base in the form of crystals or oil. The products of higher purity of these compounds may be obtained by column chromatography or recrystallization.

These free bases are easily converted to corresponding pharmaceutically acceptable acid addition salts by treatment with pharmaceutically acceptable inorganic acids such as hydrochloric, sulfuric, hydrobromic and phosphoric acids, or with pharmaceutically acceptable organic acids such as acetic, maleic, fumaric, tartaric, citric, oxalic and benzoic acids.

Names of typical examples of the compounds of this invention, their structural formulae and phycochemical properties are listed in Tables 1, 2 and 3, respectively.

The Nos. of these compounds listed in the tables (1, 2, ..., 36) correspond to the desired compounds given in Examples described hereinafter (1, 2, ..., 36).

TABLE 1

| Compound | Name |
|---|---|
| 1 | 5-[2-(Diethylamino)ethyl]amino-5,11-dihydro[1]benzoxepino[3,4-b]pyridine |
| 2 | 5-[2-(Diethylamino)ethyl]amino-7-methyl-5,11-dihydro[1]benzoxepino[3,4-b]pyridine |
| 3 | 5-[2-(Diethylamino)ethyl]amino-7-chloro-5,11-dihydro[1]benzoxepino[3,4-b]pyridine |
| 4 | 5-[2-(Diethylamino)ethyl]amino-5,11-dihydro[1]benzothiepino[3,4-b]pyridine |
| 5 | 5-[2-(Dimethylamino)ethyl]amino-5,11-dihydro-[1]benzoxepino[3,4-b]pyridine |
| 6 | 5-[2-(Dimethylamino)ethyl]amino-7-methyl-5,11-dihydro[1]benzoxepino[3,4-b]pyridine |
| 7 | 5-[3-(Diethylamino)propyl]amino-5,11-dihydro-[1]benzoxepino[3,4-b]pyridine |
| 8 | 5-[3-(Diethylamino)propyl]amino-7-methyl-5,11-dihydro[1]benzoxepino[3,4-b]pyridine |
| 9 | 5-[3-(Dimethylamino)propyl]amino-5,11-dihydro-[1]benzoxepino[3,4-b]pyridine |
| 10 | 5-[3-(Dimethylamino)propyl]amino-7-methyl-5,11-dihydro[1]benzoxepino[3,4-b]pyridine |
| 11 | 5-{N—ethyl-N—[2-(diethylamino)]ethyl}amino-5,11-dihydro[1]benzoxepino[3,4-b]pyridine |
| 12 | 5-[2-(Ethylamino)ethyl]amino-7-methyl-5,11-dihydro[1]benzoxepino[3,4-b]pyridine |
| 13 | 5-[2-(1-Pyrrolidinyl)ethyl]amino-5,11-dihydro-[1]benzoxepino[3,4-b]pyridine |
| 14 | 5-[2-(Piperidino)ethyl]amino-5,11-dihydro[1]-benzoxepino[3,4-b]pyridine |
| 15 | 5-[2-(Morpholino)ethyl]amino-5,11-dihydro[1]-benzoxepino[3,4-b]pyridine |
| 16 | 5-[2-(Amino)ethyl]amino-5,11-dihydro[1]-benzoxepino[3,4-b]pyridine |
| 17 | 5-(3-Pyridyl)amino-5,11-dihydro[1]benzoxepino-[3,4-b]pyridine |
| 18 | 5-[3-(1-Ethyl)piperidinyl]amino-5,11-dihydro-[1]benzoxepino[3,4-b]pyridine |
| 19 | 5-[3-(Cyclohexylamino)propyl]amino-5,11-dihydro-[1]benzoxepino[3,4-b]pyridine |
| 20 | 5-[1-(4-Methyl)piperazinyl]-5,11-dihydro[1]-benzoxepino[3,4-b]pyridine |
| 21 | 5-[1-(4-Methyl)piperazinyl]-7-methyl-5,11-dihydro[1]benzoxepino[3,4-b]pyridine |
| 22 | 5-[2-(Diethylamino)ethyl]amino-7-fluoro-5,11-dihydro[1]benzoxepino[3,4-b]pyridine |
| 23 | 5-[2-(Diethylamino)ethyl]amino-9-methyl-5,11-dihydro[1]benzoxepino[3,4-b]pyridine |
| 24 | 5-[2-(Diisopropylamino)ethyl]amino-5,11-dihydro-[1]benzoxepino[3,4-b]pyridine |
| 25 | 5-(3-Quinuclidinyl)amino-5,11-dihydro[1]-benzoxepino[3,4-b]pyridine |
| 26 | 5-{N—acetyl-N—[2-(diethylamino)ethyl]}amino-5,11-dihydro[1]benzoxepino[3,4-b]pyridine |
| 27 | 5,11-Dihydro-5-[(N,N—diisopropylamino)acetyl]-amino[1]benzoxepino[3,4-b]pyridine |
| 28 | 5-[(N,N—diethylamino)acetyl]amino-5,11-dihydro-[1]benzoxepino[3,4-b]pyridine |
| 29 | 5,11-Dihydro-5-[(4-methyl-1-piperazinyl)-acetyl]amino[1]benzoxepino[3,4-b]pyridine |
| 30 | 5,11-Dihydro-5-[(1-imidazoly)acetyl]amino[1]-benzoxepino[3,4-b]pyridine |
| 31 | 1-(5,11-Dihydro[1]benzoxepino[3,4-b]pyridin-5-yl)1,3-dimethylurea |
| 32 | 1-(5,11-Dihydro-7-methyl[1]benzoxepino[3,4-b]-pyridin-5-yl)1,3-dimethylurea |
| 33 | 1-(5,11-Dihydro-9-methyl[1]benzoxepino[3,4-b]-pyridin-5-yl)1,3-dimethylurea |
| 34 | 1-(5,11-Dihydro-7-fluoro[1]benzoxepino[3,4-b]-pyridin-5-yl)1,3-dimethylurea |
| 35 | 1-(5,11-Dihydro[1]benzothiepino[3,4-b]pyridin-5-yl)1,3-dimethylurea |
| 36 | 1-(5,11-Dihydro[1]benzoxepino[3,4-b]pyridin-5-yl)1,3-diethylurea |

TABLE 2

| Compound | $R^1$ | Position | X | $R^2$ |
|---|---|---|---|---|
| 1 | H | — | O | —NHCH$_2$CH$_2$N(CH$_2$CH$_3$)$_2$ |
| 2 | CH$_3$ | 7 | " | " |
| 3 | Cl | 7 | " | " |
| 4 | H | — | S | " |
| 5 | H | — | O | —NHCH$_2$CH$_2$N(CH$_3$)$_2$ |
| 6 | CH$_3$ | 7 | " | " |
| 7 | H | — | " | —NHCH$_2$CH$_2$CH$_2$N(CH$_2$CH$_3$)$_2$ |
| 8 | CH$_3$ | 7 | " | " |
| 9 | H | — | " | —NHCH$_2$CH$_2$CH$_2$N(CH$_3$)$_2$ |
| 10 | CH$_3$ | 7 | " | " |
| 11 | H | — | " | —N(CH$_2$CH$_3$)CH$_2$CH$_2$N(CH$_2$CH$_3$)$_2$ |
| 12 | CH$_3$ | 7 | " | —NHCH$_2$CH$_2$NHCH$_2$CH$_3$ |

TABLE 2-continued

Structure: pyridine-CH(R²)-phenyl(R¹ at 7,8,9)-with pyridine-CH₂-X linkage

| Compound | R¹ | Position | X | R² |
|---|---|---|---|---|
| 13 | H | — | " | —NHCH₂CH₂N(pyrrolidine) |
| 14 | " | — | " | —NHCH₂CH₂N(piperidine) |
| 15 | " | — | " | —NHCH₂CH₂N(morpholine) |
| 16 | " | — | " | —NHCH₂CH₂NH₂ |
| 17 | " | — | " | —NH(3-pyridyl) |
| 18 | " | — | " | —NH(1-ethyl-piperidin-3-yl) |
| 19 | " | — | " | HN(H)—CH₂CH₂CH₂—N(H)—cyclohexyl |
| 20 | " | — | " | —N(4-methylpiperazin-1-yl) |
| 21 | CH₃ | 7 | " | " |
| 22 | F | 7 | " | —NHCH₂CH₂N(CH₂CH₃)₂ |
| 23 | CH₃ | 9 | " | " |
| 24 | H | — | " | —NHCH₂CH₂N[CH(CH₃)₂]₂ |
| 25 | H | — | " | —NH(quinuclidin-3-yl) |
| 26 | H | — | " | CH₃CON(—)CH₂CH₂N(CH₂CH₃)₂ |
| 27 | H | — | " | —NHCOCH₂N[CH(CH₃)₂]₂ |
| 28 | H | — | " | —NHCOCH₂N(CH₂CH₃)₂ |
| 29 | H | — | " | —NHCOCH₂—N(4-methylpiperazin-1-yl)—NCH₃ |
| 30 | H | — | " | —NHCOCH₂—N(imidazol-1-yl) |
| 31 | H | — | " | CH₃N(—)CONHCH₃ |
| 32 | CH₃ | 7 | " | " |
| 33 | CH₃ | 9 | " | " |
| 34 | F | 7 | " | " |
| 35 | H | — | S | " |
| 36 | H | — | " | CH₂CH₃N(—)CONHCH₂CH₃ |

TABLE 3

| Compound | M.P. °C. | IR Spectrum (Liquid film, cm⁻¹) | NMR Spectrum (CDCl₃, δ-value, ppm) | Elemental Analysis Calc. (%) Upper / Found (%) Lower |
|---|---|---|---|---|
| 1 | Trihydrochloride/monohydrate 180–183 (dec) | 3300, 2960, 1590, 1455, 1225, 1050 | 0.93(t, 6H), 2.17–3.17(m, 9H), 4.51(s, 1H), 5.01 and 5.73 (q, 2H, AB type), 6.78–7.38 (m, 5H), 7.58(dd, 1H), 8.35 (dd, 1H) | $C_{19}H_{28}N_3OCl_3 \cdot H_2O$, (trihydrochloride/monohydrate)<br>C 52.00  H 6.89  N 9.58<br>C 52.09  H 6.96  N 9.56 |
| 2 | Trihydrochloride/hemihydride 203–208 | 3300, 2970, 1590, 1510, 1460, 1215, 820 | 0.92(t, 6H), 2.23(s, 3H), 2.02–3.62(m, 9H), 4.47(s, 1H), 5.01 and 5.65(q, 2H, AB type), 6.78–7.28(m, 4H), 7.57(dd, 1H), 8.33(dd, 1H) | $C_{20}H_{30}N_3OCl_3 \cdot 1/2H_2O$, (trihydrochloride/hemihydrate)<br>C 54.12  H 7.04  N 9.47<br>C 54.32  H 6.98  N 9.43 |
| 3 | Trihydrochloride/hemihydrate 211.5–213 (dec) | 3300, 2970, 1590, 1485, 1265, 1225 | 0.93(t, 6H), 2.18–2.91(m, 9H), 4.49(s, 1H), 5.01 and 5.68(q, 2H, AB type), 6.83–7.32(m, 4H), 7.54(dd, 1H), 8.32(dd, 1H) | $C_{19}H_{27}N_3OCl_4 \cdot 1/2H_2O$, (trihydrochloride/hemihydrate)<br>C 49.15  H 6.08  N 9.05<br>C 49.51  H 5.97  N 8.82 |
| 4 | Trihydrochloride/monohydrate 175 | 3300, 2970, 1590, 1450, 1070, 750 | 1.00(t, 6H), 2.32–2.78(m, 9H), 4.29 and 5.03(q, 2H, AB type), 5.05(s, 1H), 6.92–7.49(m, 5H), 7.64(dd, 1H), 8.33(dd, 1H) | $C_{19}H_{28}N_3SCl_3 \cdot H_2O$, (trihydrochloride/monohydrate)<br>C 50.17  H 6.65  N 9.24 |

TABLE 3-continued

| Compound | M.P. °C. | IR Spectrum (Liquid film, cm⁻¹) | NMR Spectrum (CDCl₃, δ-value, ppm) | Elemental Analysis | Calc. (%) Upper / Found (%) Lower | | |
|---|---|---|---|---|---|---|---|
| | | | | | C | H | N |
| 5 | Trihydrochloride/hemihydrate 170-175 (dec) | 3300, 2930, 1590, 1580, 1455, 1040, 755 | 1.10(s, 6H), 2.30-2.83(m, 4H), 4.52(s, 1H), 5.03 and 5.74(q, 2H, AB type), 6.80-7.33(m, 5H), 7.60(dd, 1H), 8.38(dd, 1H) | C₁₇H₂₄N₃OCl₃.1/2H₂O, (trihydrochloride/hemihydrate) | 50.00 50.82 51.19 | 6.69 6.27 6.19 | 8.89 10.46 10.49 |
| 6 | Trihydrochloride/hemihydrate Hygroscopic; not measurable | 3300, 2940, 1590, 1455, 1215, 1040 | 2.03(s, 6H), 2.23(s, 3H), 1.88-2.87(m, 5H), 4.42(s, 1H), 4.93 and 5.56(q, 2H, AB type), 6.78-7.13(m, 4H), 7.48(dd, 1H), 8.25(dd, 1H) | C₁₇H₂₀N₃OCl₃.1/2H₂O, (trihydrochloride/hemihydrate) | 52.00 52.21 | 6.5 5 6.60 | 10.11 10.06 |
| 7 | Trihydrochloride/monohydrate 159-161 (dec) | 3300, 2960, 1590, 1580, 1490, 1220, 750 | 0.91(t, 6H), 1.38-2.75(m, 10H), 4.50(s, 1H), 5.04 and 5.82(q, 2H, AB type), 6.72-7.42(m, 5H), 7.57(dd, 1H), 8.35(dd, 1H) | C₂₀H₃₀ON₃Cl₃.H₂O, (trihydrochloride/monohydrate) | 53.05 52.94 | 7.12 7.31 | 9.28 9.25 |
| 8 | Trihydrochloride/hemihydrate 193 (dec) | 3270, 2970, 1590, 1510, 1460, 1220, 1040 | 0.93(t, 6H), 1.42-3.08(m, 11H), 2.25(s, 3H), 4.42(s, 1H), 5.00 and 5.66(q, 2H, AB type), 6.62-7.42(m, 4H), 7.58(dd, 1H), 8.38(dd, 1H) | C₂₁H₃₂ON₃Cl₃.1/2H₂O, (trihydrochloride/hemihydrate) | 55.09 55.30 | 7.26 7.62 | 9.18 9.25 |
| 9 | Trihydrochloride/hemihydrate Hygroscopic; not measurable | 3250, 2930, 1590, 1575, 1455, 1045, 73 | 2.03(s, 6H), 1.98-2.65(m, 7H), 4.40(s, 1H), 4.93 and 5.65(q, 2H, AB type), 6.67-7.30(m, 5H), 7.43(dd, 1H), 8.21(dd, 1H) | C₁₈H₂₆ON₃Cl₃.1/2H₂O, (trihydrochloride/hemihydrate) | 52.00 52.06 | 6.55 6.46 | 10.11 10.23 |
| 10 | Trihydrochloride/hemihydrate Hygroscopic; not measurable | 3270, 2940, 1580, 1510, 1460, 1040, 760 | 1.32-2.97(m, 7H), 2.13(s, 6H), 2.25(s, 3H), 4.43(s, 1H), 5.01 and 5.64(q, 2H, AB type), 6.75-7.42(m, 4H), 7.60(dd, 1H), 8.38(dd, 1H) | C₁₈H₂₀N₃OCl₃.1/2H₂O, (trihydrochloride/hemihydrate) | 52.00 52.21 | 6.55 6.60 | 10.11 10.06 |
| 11 | Trihydrochloride/monohydrate 126-129 (dec) | 2970, 1580, 1490, 1455, 1220, 1015, 755 | 0.83(t, 6H), 0.94(t, 3H), 1.88-2.89(m, 10H), 4.32(s, 1H), 4.93 and 6.59(q, 2H, AB type), 6.56-7.26(m, 5H), 7.49(dd, 1H), 8.37(dd, 1H) | C₂₁H₃₂ON₃Cl₃.H₂O, (trihydrochloride/monohydrate) | 54.02 53.96 | 7.34 7.73 | 9.00 8.81 |
| 12 | Trihydrochloride/monohydrate 129 (dec) | 3320, 2940, 1590, 1460, 1215, 1045, 820 | 1.03(t, 3H), 2.0-2.9(m, 11H), 4.42(s, 1H), 4.98 and 5.60(q, 2H, AB type), 6.75-7.25(m, 4H), 7.53(dd, 1H), 8.31(dd, 1H) | C₁₈H₂₆ON₃Cl₃.H₂O, (trihydrochloride/monohydrate) | 50.89 50.58 | 6.64 6.70 | 9.89 9.78 |
| 13 | Trihydrochloride/hemihydrate 155-160 (dec) | 3300, 2950, 1590, 1580, 490, 1450, 1220 | 2.38-3.20(m, 12H), 4.34(s, 1H), 4.87 and 5.58(q, 2H, AB type), 6.78-7.28(m, 5H), 7.44 (dd, 1H), 8.21(dd, 1H) | C₁₉H₂₆N₃OCl₃.1/2H₂O, (trihydrochloride/hemihydrate) | 53.34 53.34 | 6.36 6.62 | 9.82 9.85 |
| 14 | Trihydrochloride/monohydrate 190-195 (dec) | 3300, 2930, 1590, 1580, 1490, 1450, 755 | 0.91-1.79(m, 6H), 1.83-2.83 (m, 9H), 4.48(s, 1H), 5.00 and 5.69(q, 2H, AB type), 6.79-7.43 (m, 5H), 7.55(dd, 1H), 8.31(dd, 1H) | C₂₀H₃₀N₃O₂Cl₃, (trihydrochloride/monohydrate) | 53.28 53.48 | 6.71 6.63 | 9.32 9.23 |
| 15 | Trihydrochloride/monohydrate 199-204 (dec) | 3300, 1590, 1580, 1490, 1460, 1120, 1040 | 2.11-2.69(m, 8H), 3.46-3.68 (m, 4H), 4.39(s, 1H), 4,95 and 5.59(q, 2H, AB type), 6.86-7.31 (m, 5H), 7.52(dd, 1H), 8.28(dd, 1H) | C₁₉H₂₆N₃O₂Cl₃.H₂O, (trihydrochloride/monohydrate) | 50.40 50.79 | 6.23 6.14 | 9.28 9.48 |
| 16 | Trihydrochloride/hemihydrate 180 (dec) | 3280, 2940, 1590, 1580, 1455, 1040, 755 | 2.28-2.91(m, 4H), 4.48(s, 1H), 5.00 and 5.70(q, 2H, AB type), 6.7-7.4(m, 5H), 7.58(dd, 1H), 8.33(dd, 1H) | C₁₅H₂₀N₃OCl₃.1/2H₂O, (trihydrochloride/hemihydrate) | 48.21 48.59 | 5.66 5.79 | 11.24 10.88 |
| 17 | 132-136 | 1580, 1485, 1220, 1110, 1040, 800 | 5.10 and 5.50(q, 2H, AB type), 5.36(s, 1H), 6.9-8.5(m, 11H) | C₁₈H₁₅N₃O | 74.72 74.46 | 5.23 5.06 | 14.52 14.62 |
| 18 | Trihydrochloride/dihydrate (diastereoisomeric mixt.) 165-170 (dec) | 3300, 2930, 1590, 1450, 1265, 1210, 1045 | 0.83-3.00(m, 14H), 4.62(s, 1H), [5.00 and 5.74(q, AB type)] and [5.00 and 5.80(q, AB type)] (total 2H), 6.83-7.37(m, 5H), 7.58(dd, 1H), 8.36(dd, 1H) | C₂₀H₂₈N₃OCl₃.2H₂O, (trihydrochloride/dihydrate) | 51.24 51.48 | 6.88 6.95 | 8.96 8.90 |
| 19 | Trihydrochloride/monohydrate 240-243 (dec) | 3275, 2920, 1590, 1580, 1450, 1220, 750 | 0.5-2.9(m, 19H), 4.43(s, 1H), 4.95 and 5.65(q, 2H, AB type), 6.5-7.3(m, 5H), 7.48(dd, 1H), 8.23(dd, 1H) | C₂₂H₃₂N₃OCl₃.H₂O, (trihydrochloride/monohydrate) | 55.18 55.35 | 7.16 7.05 | 8.77 8.90 |
| 20 | 100-102 | KBr tablet, cm⁻¹ 2800, 1585, | 2.23(s, 3H), 2.38(br, s, 8H), 3.92(s, 1H), 4.95 and 6.63(q, 2H, AB type), 6.50-7.68(m, | C₁₈H₂₁N₃O | 73.19 | 7.17 | 14.23 |

TABLE 3-continued

| Compound | M.P. °C. | IR Spectrum (Liquid film, cm$^{-1}$) | NMR Spectrum (CDCl$_3$, δ-value, ppm) | Elemental Analysis | Calc. (%) Upper / Found (%) Lower | | |
|---|---|---|---|---|---|---|---|
| | | 1490, 1455, 1220, 1145, 755 | 1H), 8.47(dd, 1H) | | 73.34 | 7.27 | 14.07 |
| 21 | 115–118 | KBr tablet, cm$^{-1}$ 2800, 1580, 1500, 1460, 1220, 1150 | 2.22(br, s, 6H), 2.33(br, s, 8H), 3.85(s, 1H), 4.90 and 6.52(q, 2H, AB type), 6.6–7.3 (m, 4H), 7.48(dd, 1H), 8.42 (dd, 1H) | C$_{19}$H$_{23}$N$_3$O | C 73.76 73.87 | H 7.49 7.56 | N 13.58 13.38 |
| 22 | Trihydrochloride/hemihydrate 212–215 (dec) | 3300, 2960, 2800, 1495, 1200, 1040, 780 | 0.95(t, 3H), 2.42(q, 2H), 2.55(br, s, 4H), 4.55(s, 1H), 5.05 and 5.55(q., 2H, AB type), 6.7–7.4(m, 4H), 7.65(dd, 1H), 8.39(dd, 1H) | C$_{19}$H$_{27}$N$_3$OF.1/2H$_2$O, (trihydrochloride/hemihydrate) C 50.96 51.22 | H 6.30 6.42 | N 9.38 9.43 | |
| 23 | Trihydrochloride/2.5-hydrate 180 (dec) | 3300, 2960, 2800, 1470, 1450, 1200, 770 | 0.93(t, 1H), 2.2–2.8(m, 11H), 4.52(s, 1H), 5.00 and 5.54(q, 2H, AB type), 6.7–7.2(m, 4H), 7.62(dd, 1H), 8.35(dd, 1H) | C$_{20}$H$_{30}$N$_3$OCl$_3$.2.5H$_2$O, (trihydrochloride/2.5-hydrate) C 50.06 50.39 | H 7.35 7.70 | N 8.76 8.62 | |
| 24 | Trihydrochloride/hemihydrate 190–200 (dec) | 3280, 2960, 1590, 1580, 1455, 1040, 755 | 0.91(d, 12H), 2.4–3.1(m, 7H), 4.54(s, 1H), 5.07–5.54(q, 2H, AB type), 6.9–7.3(m, 5H), 7.63(dd, 1H), 8.40(dd, 1H) | C$_{21}$H$_{32}$N$_3$OCl$_3$.1/2H$_2$O, (trihydrochloride/hemihydrate) C 55.09 54.98 | H 7.26 7.39 | N 9.18 9.03 | |
| 25 | Trihydrochloride/monohydrate (diastereoisomeric mixt.) 180 (dec) | CHCl$_3$ soln, cm$^{-1}$ 3325, 2930, 1590, 1580, 1455, 1210, 1045 | 0.80–3.38(m, 13H), 4.50(br, s, 1H), [5.01 and 5.65(q, AB type)] and [5.01 and 5.75(q, AB type)] (total 2H), 6.80–7.30 (m, 5H), 7.56(br, d, 1H), 8.36(dd, 1H) | C$_2$OH$_{26}$N$_3$OCl$_3$.H$_2$O, (trihydrochloride/monohydrate) C 53.52 53.61 | H 6.29 6.69 | N 9.36 9.39 | |
| 26 | Dihydrochloride/monohydrate 87–90 | 2950, 1640, 1490, 1405, 1210, 1040 | 0.82(t, 6H), 1.65–2.82(m, 6H), 2.17(s, 3H), 3.28–3.72(m, 2H), 5.00 and 5.35(q, 2H, AB type), 6.82–7.57(m, 5H), 7.76(dd, 1H), 8.37(dd, 1H) | C$_{21}$H$_{29}$N$_3$O$_2$Cl$_2$.H$_2$O, (dihydrochloride/monohydrate) C 56.70 57.01 | H 7.03 7.39 | N 9.46 9.23 | |
| 27 | 117–119 | 3320, 2970, 1660, 1490, 1220, 770 (KBr tablet) | 0.85(d, 12H), 2.63–3.13(m, 2H), 2.98(s, 2H), 5.07 and 5.50(q, 2H, AB type), 5.98(d, 1H), 6.87–7.53(m, 5H), 7.85(dd, 1H), 8.43(dd, 1H), 8.78(br, 1H) | C$_{21}$H$_{27}$N$_3$O$_2$ C 71.36 71.07 | H 7.70 7.79 | N 11.89 12.23 | |
| 28 | Hygroscopic; not measurable (monofumarate/1,5-hydrate) | 3350, 2960, 1670, 1490, 1200, 1040 (Liquid film) | 0.87(t, 6H), 2.40(q, 4H), 2.93 (s, 2H), 5.02 and 5.47(q, 2H, AB type), 4.98(d, 1H), 6.87–7.57(m, 5H), 7.78(dd, 1H), 8.27–8.67(m, 2H) | C$_{23}$H$_{27}$N$_3$O$_6$.1.5H$_2$O (monofumarate/1.5-hydrate) C 58.96 59.18 | H 6.45 6.07 | N 8.97 8.57 | |
| 29 | 148–153 (dec) (monofumarate/1.5-hydrate) | 3350, 2930, 2800, 1670, 1490, 1450, 750 (Liquid film) | 2.22(s, 3H), 2.32(s, 8H), 2.90(s, 2H), 5.03 and 5.48(q, 2H, AB type), 5.98(d, 1H), 6.87–7.10(m, 5H), 7.80(dd, 1H), 8.28–8.63(m, 2H) | C$_{24}$H$_{26}$N$_4$O$_6$.1.5H$_2$O (monofumarate/1.5-hydrate) C 58.17 58.25 | H 6.31 6.15 | N 11.31 10.97 | |
| 30 | 184–186 (dec) | 3400, 1670, 1520, 1495, 1215, 770 (KBr tablet) | 4.53(s, 2H), 4.95 and 5.38 (q, 2H, AB type), 5.96(d, 1H), 6.82–7.58(m, 8H), 7.80(dd, 1H), 8.43(dd, 1H) | C$_{18}$H$_{16}$N$_4$O$_2$ C 67.49 67.24 | H 5.03 4.89 | N 17.49 17.58 | |
| 31 | 158.5–160 | 3340, 2950, 1620, 1540, 1310, 775 (KBr tablet) | 2.72(s, 3H), 2.84(d, 3H), 4.55 (br, 1H), 5.07 and 5.37(q, 2H, AB type), 6.98(s, 1H), 6.88–7.65(m, 5H), 7.88(dd, 1H), 8.46(dd, 1H) | C$_{16}$H$_{17}$N$_3$O$_2$ C 67.83 67.85 | H 6.05 6.04 | N 14.83 14.86 | |
| 32 | 153–155 | 3320, 1620, 1540, 1310, 1220, 1030 (KBr tablet) | 2.27(s, 3H), 2.73(s, 3H), 2.83 (d, 3H), 4.70(br, 1H), 4.98 and 5.32(q, 2H, AB type), 6.90–7.25 (m, 5H), 7.83(dd, 1H), 8.38(dd, 1H) | C$_{17}$H$_{19}$N$_3$O$_2$ C 68.67 68.40 | H 6.44 6.43 | N 14.13 14.10 | |
| 33 | 192–195 | 3380, 2955, 1620, 1530, 1310, 770 (KBr tablet) | 2.32(s, 3H), 2.73(s, 3H), 2.80 (d, 3H), 4.57(br, 1H), 4.95 and 5.34(q, 2H, AB type), 6.78–7.48 (m, 5H), 7.82(dd, 1H), 8.39(dd, 1H) | C$_{17}$H$_{19}$N$_3$O$_2$ C 68.67 68.54 | H 6.44 6.47 | N 14.13 14.00 | |
| 34 | 112–114 | 3350, 2945, 1620, 1490, 1360, 1300, 820 (KBr tablet) | 2.70(s, 3H), 2.81(d, 3H), 4.68 (br, 1H), 5.00 and 5.30(q, 2H, AB type), 6.72–7.42(m, 5H), 7.78(dd, 1H), 8.37(dd, 1H) | C$_{16}$H$_{16}$N$_3$O$_2$F C 63.78 63.39 | H 5.35 5.61 | N 13.95 13.87 | |
| 35 | 176–178 | 3320, 1625, 1550, 1330, 1190, 760 (KBr tablet) | 2.73(d, 3H), 2.80(s, 3H), 3.90 and 4.70(q, 2H, AB type), 4.60 (br, 1H), 6.20(s, 1H), 6.93–7.43 (m, 5H), 7.68(dd, 1H), 8.31(dd, 1H) | C$_{16}$H$_{17}$N$_3$OS C 64.19 64.09 | H 5.72 5.73 | N 14.04 13.80 | |

TABLE 3-continued

| Compound | M.P. °C. | IR Spectrum (Liquid film, cm$^{-1}$) | NMR Spectrum (CDCl$_3$, δ-value, ppm) | Elemental Analysis | Calc. (%) Upper / Found (%) Lower | | |
|---|---|---|---|---|---|---|---|
| 36 | 92-93 | 3400, 2970, 1620, 1525, 1270, 1220, 775 (KBr tablet) | 0.73(t, 3H), 1.12(t, 3H), 3.02-3.58(m, 4H), 4.32(br, 1H), 5.04 and 5.30(q, 2H, AB type), 6.82-7.65(m, 6H), 7.87 (dd, 1H), 8.37(dd, 1H) | C$_{18}$H$_{21}$N$_3$O$_2$ | C<br>69.43<br>69.67 | H<br>6.80<br>6.83 | N<br>13.50<br>13.57 |

Test methods for acute toxicity and antiulcer activity of the present compounds are described below.

Test for acute toxicity

Groups of 5 male dd-strain mice weighing 19 to 21 g were used. The present compounds were administered either orally (0.3 mg/g) or intraperitoneally (0.1 mg/g). The MLD (minimum lethal dose) was determined by observing the mortality for 7 days after the administration. Results for typical examples of the present compounds are given in Table 4.

Test for antiulcer activity

Male Donryu-strain rats weighing 190 to 210 g were starved for 17 hours prior to the test.

Immediately, after an oral administration of the present compounds (30 mg/kg or 100 mg/kg), the rats were immobilized in the stress cage devised by Takagi et al. [Jap. J. Pharmacol., 18, 9 (1968)]. The cage was then immersed vertically in a water bath at 23±1° C. for 7 hours to the height of xiphoid process.

Each rat was then killed with carbon dioxide gas and its stomach was removed. The lengths of the lesions developed on the glandular stomach were summed to give a lesion index for each rat.

Four or five rats were used for each group. The test compounds were dissolved in saline or dissolved or suspended in saline with a suitable amount of polyethylene glycol-400 added or not added. The ulcer-inhibition rate of each compound was calculated from the following formula by comparing the lesion index of the test group with that of the control group [administered with only the solvent (saline with polyethylene glycol-400 added or not added)]. Results for typical examples of the present compounds are given in Table 4.

$$\text{Inhibition Rate (\%)} = \frac{\text{(Control Group)} - \text{(Test Group)}}{\text{(Control Group)}} \times 100$$

TABLE 4

| Compound | Acute MLD (mg/kg) po | Acute MLD (mg/kg) ip | Ulcer-inhibition Rate (%) | Dose | |
|---|---|---|---|---|---|
| 1* | >300 | >100 | 85 | po: | 30 mg/kg |
| 5* | >300 | >100 | 78 | | 30 |
| 7* | >300 | >100 | 55 | | 30 |
| 13* | >300 | >100 | 72 | | 30 |
| 15* | >300 | >100 | 73 | | 30 |
| 20 | >300 | >100 | 67 | | 30 |
| 24* | >300 | >100 | 88 | | 30 |
| 27 | >300 | >100 | 79 | po: | 100 mg/kg |
| 28** | >300 | >100 | 98 | | 100 |
| 29** | >300 | >100 | 64 | | 100 |
| 31 | >300 | >100 | 93 | | 100 |
| 36 | >300 | >100 | 81 | | 100 |

*administered in a form of hydrochloride
**administered in a form of fumarate

As is appearent from the results of Table 4, the present compounds have excellent antiulcer activity, and therefore are useful as an antiulcer agent.

The present compounds may be used in various pharmaceutical forms for administration. Pharmaceutical compositions of the present invention are prepared by uniformly mixing an effective amount of present compounds as the active ingredient, in free form or as an acid addition salt, with a pharmaceutically acceptable carrier.

The carrier may take various forms depending on the pharmaceutical form suitable for administration. It is preferable that the pharmaceutical composition is in single administration form suitable for administration orally or by injection.

To prepare the compositions of the present invention for oral administration, any useful pharmaceutical carrier may be used. For example, oral liquid preparations such as suspensions and syrups can be prepared using water, sugar (e.g. sucrose, sorbitol and fructose), glycols (e.g. polyethyleneglycol and propyleneglycol), oils (e.g. sesame oil, olive oil and soybean oil), antisepics (e.g. an alkyl parahydroxybenzoate), flavours (e.g. strawberry flavour and peppermint) and the like. Powders, pills, capsules and tablets can be prepared using excipients (e.g. lactose, glucose, sucrose and mannitol), disintegrators (e.g. starch and sodium alginate), lubricants (e.g. magnesium stearate and talc), binders (e.g. polyvinyl alcohol, hydroxypropylcellulose and gelatin), surfactants (e.g. sucrose fatty acid ester), plasticizers (e.g. glycerin) and the like.

Tablets and capsules are the most useful single oral administration forms because of the ease of administration. To make tablets and capsules solid pharmaceutical carriers are used.

An injection solution can be prepared using a carrier consisting of salt solution, glucose solution and a mixture of salt and glucose solution.

Although the amount of the active ingredient can be varied over a rather wide range, 10–50 mg person (about 60 kg)/day in one dose or several divided doses is generally considered to be effective.

Certain specific embodiments of the invention are illustrated by the following representative examples.

The melting point, IR spectrum, NMR spectrum and elemental analysis of the compound obtained in each Example are given in Table 3.

EXAMPLE 1

In this example, 11.1 g of 5-oxo-5,11-dihydro-[1]benzoxepino[3,4-b]pyridine was dissolved in 160 ml of ethanol and 1.3 g of sodium borohydride was added thereto. The mixture was stirred at room temperature for 3 hours. The reaction solution was concentrated under reduced pressure to distill away ethanol. Then, 50 ml of water and 100 ml of ethyl acetate were added to the residue and the mixture was shaken. The separated aqueous layer was removed, and the ethyl acetate layer was dried and concentrated under reduced pressure, whereby 10.5 g of 5-hydroxy-5,11-dihydro[1]benzoxepino[3,4-b]pyridine as crude crystals was obtained. Recrystallization from isopropanol gave 9.5 g of pure crystals.

Melting point: 143°–144° C.

IR spectrum: (KBr tablet, cm$^{-1}$) 3200, 1590, 1485, 1215, 1040, 800.

NMR spectrum: (CDCl$_3$, δ-value, ppm) 5.19 and 5.42(ABq, 2H), 5.78(s, 1H), 6.95–7.60(m, 5H), 7.80(dd, 1H), 8.33(dd, 1H).

Elemental analysis: (as C$_{13}$H$_{11}$NO$_2$)(%)

|  | C | H | N |
|---|---|---|---|
| Calculated: | 73.23 | 5.20 | 6.57 |
| Found: | 73.01 | 5.04 | 6.48 |

Then, 1.5 g of 5-hydroxy-5,11-dihydro[1]benzoxepino[3,4-b]pyridine thus obtained was suspended in 15 ml of dichloromethane and a solution of 1.7 g thionyl chloride in 5 ml of dichloromethane was added thereto under ice cooling over a period of 10 minutes. The resultant solution was stirred at room temperature for one hour. The reaction solution is concentrated under reduced pressure to distill away dichloromethane and excess thionyl chloride, whereby 5-chloro-5,11-dihydro[1]benzoxepino[3,4-b]pyridine hydrochloride was obtained as residue.

This product was dissolved in 10 ml of dichloromethane. The resultant solution was added dropwise to a solution of 4.2 g of N,N-diethylethylenediamine in 20 ml of dichloromethane and the mixture was stirred at room temperature for 3 hours. Then, 20 ml of water and 20 ml of dichloromethane were added thereto and the mixture was shaken. The separated aqueous layer was removed, and the dichloromethane layer was dried and concentrated under reduced pressure. The residue was purified by chromatography on silica gel, and the main fraction was concentrated to give 2.0 g of 5-[2-(diethylamino)ethyl]amino-5,11-dihydro[1]benzoxepino[3,4-b]pyridine (compound 1) as an oily free base (yield: 91%)

This product was dissolved in isopropanol, and a solution of hydrogen chloride in isopropanol was added thereto, whereby 2.6 g of trihydrochloride.monohydrate of compound 1 was obtained.

EXAMPLES 2–23

Compounds 2 through 23 were obtained in a similar manner to that in Example 1 except that materials listed in Table 5 were used instead of 1.5 g of 5-hydroxy-5,11-dihydro[1]benzoxepino[3,4-b]pyridine and 4.2 g of N,N-diethyl-ethylenediamine.

TABLE 5

| | Material | | Compound | | |
|---|---|---|---|---|---|
| Example | Name | Used Amount (g) | No. | Obtained Amount (g) | Yield (%) |
| 2 | 5-Hydroxy-7-methyl-5,11-dihydro[1]benzoxepino-[3,4-b]pyridine | 1.8 | 2 | 2.4 | 93 |
|  | N,N—diethylethylene-diamine | 4.6 | | | |
| 3 | 5-Hydroxy-7-chloro-5,11-dihydro[1]benzoxepino-[3,4-b]pyridine | 0.8 | 3 | 0.9 | 83 |
|  | N,N—diethylethylene-diamine | 1.8 | | | |
| 4 | 5-Hydroxy-5,11-dihydro-[1]benzothiepino[3,4-b]-pyridine | 1.5 | 4 | 1.7 | 79 |
|  | N,N—dimethylethylene-diamine | 3.8 | | | |
| 5 | 5-Hydroxy-5,11-dihydro-[1]benzoxepino[3,4-b]-pyridine | 1.0 | 5 | 0.7 | 53 |
|  | N,N—dimethylethylene-diamine | 1.8 | | | |
| 6 | 5-Hydroxy-7-methyl-5,11-dihydro[1]benzoxepino-[3,4-b]pyridine | 2.3 | 6 | 1.6 | 54 |
|  | N,N—dimethylethylene-diamine | 4.4 | | | |
| 7 | 5-Hydroxy-5,11-dihydro-[1]benzoxepino[3,4-b]-pyridine | 1.8 | 7 | 2.0 | 72 |
|  | 3-Diethylaminopropyl-amine | 5.5 | | | |
| 8 | 5-Hydroxy-7-methyl-5,11-dihydro[1]benzoxepino-[3,4-b]pyridine | 2.0 | 8 | 2.7 | 80 |
|  | 3-Diethylaminopropyl-amine | 5.7 | | | |
| 9 | 5-Hydroxy-5,11-dihydro-[1]benzoxepino[3,4-b]-pyridine | 1.3 | 9 | 1.0 | 56 |
|  | 3-Dimethylaminopropyl-amine | 3.0 | | | |
| 10 | 5-Hydroxy-7-methyl-5,11-dihydro[1]benzoxepino-[3,4-b]pyridine | 2.0 | 10 | 1.1 | 40 |
|  | 3-Dimethylaminopropyl-amine | 4.5 | | | |
| 11 | 5-Hydroxy-5,11-dihydro-[1]benzoxepino[3,4-b]-pyridine | 1.5 | 11 | 1.8 | 75 |
|  | N,N,N'—triethylethylene-diamine | 5.1 | | | |
| 12 | 5-Hydroxy-7-methyl-5,11-dihydro[1]benzoxepino-[3,4-b]pyridine | 2.3 | 12 | 1.6 | 54 |
|  | N—ethylethylenediamine | 2.7 | | | |
| 13 | 5-Hydroxy-5,11-dihydro-[1]benzoxepino[3,4-b]-pyridine | 1.5 | 13 | 2.1 | 95 |
|  | N—(2-aminoethyl)-pyrrolidine | 4.0 | | | |
| 14 | 5-Hydroxy-5,11-dihydro-[1]benzoxepino[3,4-b]-pyridine | 2.0 | 14 | 2.3 | 76 |
|  | N—(2-aminoethyl)-piperidine | 6.0 | | | |
| 15 | 5-Hydroxy-5,11-dihydro-[1]benzoxepino[3,4-b]-pyridine | 2.0 | 15 | 2.6 | 85 |
|  | N—(2-aminoethyl)-morpholine | 2.4 | | | |
| 16 | 5-Hydroxy-5,11-dihydro-[1]benzoxepino[3,4-b]-pyridine | 2.0 | 16 | 2.0 | 84 |
|  | Ethylenediamine | 5.6 | | | |
| 17 | 5-Hydroxy-5,11-dihydro-[1]benzoxepino[3,4-b]-pyridine | 2.0 | 17 | 1.6 | 59 |
|  | 3-Aminopyridine | 1.8 | | | |
| 18 | 5-Hydroxy-5,11-dihydro-[1]benzoxepino[3,4-b]-pyridine | 2.0 | 18 | 2.1 | 69 |
|  | 3-Amino-N—ethyl-piperidine | 2.4 | | | |
| 19 | 5-Hydroxy-5,11-dihydro-[1]benzoxepino[3,4-b]-pyridine | 2.0 | 19 | 1.9 | 57 |

TABLE 5-continued

| Ex- am- ple | Material Name | Used A- mount (g) | Compound No. | Obtained Amount (g) | Yield (%) |
|---|---|---|---|---|---|
| | N—(3-aminopropyl)- cyclohexylamine | 4.4 | | | |
| 20 | 5-Hydroxy-5,11-dihydro- [1]benzoxepino[3,4-b]- pyridine | 1.35 | 20 | 1.7 | 76 |
| | N—methylpiperazine | 3.1 | | | |
| 21 | 5-Hydroxy-7-methyl-5,11- dihydro[1]benzoxepino- [3,4-b]pyridine | 1.8 | 21 | 1.6 | 65 |
| | N—methylpiperazine | 4.0 | | | |
| 22 | 5-Hydroxy-7-fluoro-5,11- dihydro[1]benzoxepino- [3,4-b]pyridine | 2.0 | 22 | 1.8 | 63 |
| | N—N—diethylethylenedi- amine | 3.5 | | | |
| 23 | 5-Hydroxy-9-methyl-5,11- dihydro[1]benzoxepino- [3,4-b]pyridine | 2.0 | 23 | 1.6 | 56 |
| | N,N—diethylethylenedi- amine | 3.5 | | | |

EXAMPLE 24

In this example, hydrochloride of 5-chloro-5,11-dihydro[1]benzoxepino[3,4-b]pyridine prepared from 4.3 g of 5-hydroxy-5,11-dihydro[1]benzoxepino[3,4-b]pyridine in a similar manner to that in Example 1 was dissolved in 50 ml of dichloromethane. The mixture solution was added dropwise to a 200 ml solution of ammonia in dichloromethane under ice cooling, and the mixture was stirred at room temperature for 2 hours. After completion of the reaction, 50 ml of water was added thereto and the mixture was shaken. The separated aqueous layer was removed, and the dichloromethane layer was dried and concentrated under reduced pressure, whereby crude crystals of 4.2 g of 5-amino-5,11-dihydro[1]benzoxepino[3,4-b]pyridine was obtained. This product was recrystallized from diisopropyl ether to afford 3.6 g of pure crystals.

Melting point: 72°-73° C.

IR spectrum: (KBr tablet, cm$^{-1}$) 3280, 1590, 1490, 1430, 1220, 1050, 770.

NMR spectrum: (CDCl$_3$, δ-value, ppm) 4.92(s, 1H), 5.11 and 5.52(q, 2H, AB type), 6.90-7.47(m, 5H), 7.65(dd, 1H), 8.37(dd, 1H).

Elemental analysis (as C$_{13}$H$_{12}$N$_2$O)(%):

| | C | H | N |
|---|---|---|---|
| Calculated: | 73.56 | 5.70 | 13.20 |
| Found: | 73.56 | 5.54 | 13.33 |

Then, 2.0 g of 5-amino-5,11-dihydro[1]benzoxepino[3,4-b]pyridine thus obtained, 2.8 g of hydrochloride of 2-diisopropylaminoethyl chloride and 3.9 ml of triethylamine were dissolved in 35 ml of toluene. Further, 0.2 g of sodium iodide was added thereto, and the mixture was heated under reflux for 3 hours. After completion of the reaction, 35 ml of toluene and 20 ml of water were added thereto and the mixtue was shaken. The aqueous layer was removed, and the toluene layer was dried and concentrated under reduced pressure. The residue was purified by column chromatography on silica gel, and the main fraction was concentrated, whereby 2.2 g of 5-[2-(diisopropylamino)ethyl]amino-5,11-dihydro[1]benzoxepino[3,4-b]pyridine (compound 24) as oily free base was obtained. (yield: 69%)

EXAMPLE 25

In this example, 2.1 g of 5-oxo-5,11-dihydro[1]benzoxepino[3,4-b]pyridine and 8.8 g of 3-aminoquinuclidine were dissolved in 50 ml of anhydrous benzene. Then, a solution of 1.1 g of titanium tetrachloride in 20 ml of anhydrous benzene was added dropwise thereto under ice cooling. The mixture was stirred under ice cooling for 3 hours and at room temperature for an additional two days. After completion of the reaction, the precipitate formed was filtered away, and the filtrate was concentrated under the reduced pressure. Then, 150 ml of ethyl acetate and 30 ml of water were added thereto and the mixture was shaken. The separated aqueous layer was removed, and the ethyl acetate layer was dried and concentrated. Purification of the residue by chromatography on silica gel, followed by concentration of the main fraction, gave 1.35 g of 5-(3-quinuclidinyl)imino-5,11-dihydro[1]benzoxepino[3,4-b]pyridine as crystals. This product was dissolved in 20 ml of methanol and pH of the solution was adjusted to 5 with hydrochloric acid. Then, 1.0 g of sodium borocyanohydride was added thereto, and the mixture was heated at 40°-50° C. for 8 hours. After addition of 30 ml water, pH was adjusted to 12 with 1N aqueous sodium hydroxide solution, and the alkaline solution was extracted twice with 100 ml ethyl acetate. The ethyl acetate layer was dried and concentrated under reduced pressure, and the residue was purified by chromatography on silica gel. The main fraction was concentrated, whereby 1.0 g of 5-(3-quinuclidinyl)amino-5,11-dihydro[1]benzoxepino[3,4-b]pyridine (compound 25) as a diastereomeric mixture was obtained.

EXAMPLE 26

In this example, 2.1 g of 5-[2-(diethylamino)ethyl]amino-5,11-dihydro[1]benzoxepino[3,4-b]pyridine (compound 1) prepared in Example 1 and 1.0 ml of triethylamine were dissolved in 50 ml of dichloromethane. Then, 0.6 g of acetyl chloride was added dropwise thereto under ice cooling and the mixture was stirred at room temperature for one hour. After completion of the reaction, 20 ml of water was added thereto and the mixture was shaken. The separated aqueous layer was removed, and the dichloromethane layer was dried and concentrated under reduced pressure, whereby 2.1 g of 5{N-acetyl-N-[2-(diethylamino)ethyl]}amino-5,11-dihydro[1]benzoxepino[3,4-b]pyridine (compound 26) as oily free base was obtained (Yield: 91%).

EXAMPLE 27

In this example, 1.9 g of 5-amino-5,11-dihydro[1]benzoxepino[3,4-b]pyridine prepared in a similar manner to that in Example 24 and 0.9 g of triethylamine were dissolved in 30 ml of dichloromethane. A solution of 1.0 g of chloroacetyl chloride in 5 ml of dichloromethane was added dropwise thereto under ice cooling. The mixture was stirred under ice cooling for 2 hours, and concentrated under reduced pressure to distill away about two thirds of the dichloromethane. Then, 40 ml of diisopropyl ether and 10 ml of water were added thereto, and the mixture was stirred and filtered. Drying the residue gave 2.3 g of 5-(chloroacetyl)amino-5,11-dihydro[1]benzoxepino[3,4-b]pyridine as crude crystals.

This product and 3.9 g of diisopropyl amine were dissolved in 40 ml toluene. Then, 0.25 g of potassium iodide was added thereto and the mixture was heated under reflux for 8 hours. Further, 60 ml of ethyl acetate and 20 ml of water were added thereto, and the mixture was shaken. The aqueous layer was removed, and the organic layer was dried and concentrated under reduced pressure, whereby 2.3 g of 5,11-dihydro-5-[(N,N-diisopropylamino)acetyl]amino-[1]benzoxepino[3,4-b]pyridine (compound 27) as crude crystals was obtained. Recrystallization from n-hexane afforded 1.9 g of pure crystals.

EXAMPLE 28-30

Compounds 28 through 30 were obtained in a similar manner to that in Example 27 except that the amines shown in Table 6 were used instead of diisopropylamine.

TABLE 6

| | Material | | Compound | |
|---|---|---|---|---|
| Example | Name | Used Amount (g) | No. | Obtained Amount (g) |
| 28 | 5-Amino-5,11-dihydro[1]-benzoxepino[3,4-b]pyridine | 2.0 | 28 | 3.1 |
| | Diethylamine | 3.6 | | |
| 29 | 5-Amino-5,11-dihydro[1]-benzoxepino[3,4-b]pyridine | 2.2 | 29 | 3.0 |
| | N—methylpiperazine | 3.0 | | |
| 30 | 5-Amino-5,11-dihydro[1]-benzoxepino[3,4-b]pyridine | 1.7 | 30 | 1.6 |
| | Imidiazole | 1.7 | | |

EXAMPLE 31

In this example, 5-chloro-5,11-dihydro-[1]benzoxepino[3,4-b]pyridine hydrochloride, obtained from 1.7 g of 5,11-dihydro-5-hydroxy-[1]benzoxepino[3,4-b]pyridine in a similar manner to that in Example 27, was dissolved in 15 ml of dichloromethane. The resultant solution was added dropwise to a solution of 1.4 g 1,3-dimethylurea and 2.5 g of triethylamine in 35 ml of dichloromethane. The mixture was stirred at room temperature for 2 hours and concentrated under reduced pressure. Then, 100 ml of ethyl acetate and 20 ml of water were added to the residue and the mixture was shaken. The separated aqueous layer was removed, the ethyl acetate layer was washed twice with water, dried and concentrated under reduced pressure, whereby 2.2 g of 1-(5,11-dihydro[1]benzoxepino[3,4-b]pyridin-5-yl)-1,3-dimethylurea (compound 31) as crude crystals was obtained. Recrystallization from toluene afforded 1.8 g of pure crystals.

EXAMPLES 32-36

Compounds listed in Table 7 were obtained in a similar manner to that in Example 31 except that materials shown in Table 7 were used instead of 5,11-dihydro[1-]benzoxepino[3,4-b]pyridine and 1,3-dimethylurea.

TABLE 7

| | Material | | Compound | |
|---|---|---|---|---|
| Example | Name | Used Amount (g) | No. | Obtained Amount (g) |
| 32 | 5,11-Dihydro-5-hydroxy-7-methyl[1]benzoxepino-[3,4-b]pyridine | 2.0 | 32 | 1.6 |
| | 1,3-Dimethylurea | 1.5 | | |
| 33 | 5,11-Dihydro-5-hydroxy-9-methyl[1]benzoxepino-[3,4-b]pyridine | 2.0 | 33 | 1.8 |

TABLE 7-continued

| | Material | | Compound | |
|---|---|---|---|---|
| Example | Name | Used Amount (g) | No. | Obtained Amount (g) |
| | 1,3-Dimethylurea | 1.5 | | |
| 34 | 5,11-Dihydro-7-fluoro-5-hydroxy[1]benzoxepino-[3,4-b]pyridine | 2.0 | 34 | 1.1 |
| | 1,3-Dimethylurea | 1.5 | | |
| 35 | 5,11- Dihydro-5-hydroxy[1]-benzothiepino[3,4-b]-pyridine | 1.0 | 35 | 0.9 |
| | 1,3-Dimethylurea | 0.8 | | |
| 36 | 5,11-Dihydro-5-hydroxy[1]-benzoxepino[3,4-b]pyridine | 2.9 | 36 | 3.4 |
| | 1,3-Diethylurea | 3.2 | | |

EXAMPLE 37

Preparation of tablet

A tablet comprising the following components is prepared in a conventional manner.

| Component | |
|---|---|
| 5-[2-(Diethylamino)ethyl]amino-5,11-dihydro[1]-benzoxepino[3,4-b]pyrine trihydrochloride/monohydrate (trihydrochloride/monohydrate of compound 1) | 20 mg |
| Lactose | 60 mg |
| Potato starch | 30 mg |
| Polyvinyl alcohol | 2 mg |
| Magnesium stearate | 1 mg |
| Tar pigment q.s. | |

EXAMPLE 38

Preparation of tablet

A procedure similar to that in Example 37 was employed except that 25 mg of 1-(5,11-dihydro[1]benzoxepino[3,4-b]pyridin-5-yl)1,3-dimethylurea (compound 31) was used instead of 20 mg of trihydrochloride/monohydrate of compound 1.

EXAMPLE 39

Preparation of powder

A powder comprising the following components is prepared in a conventional manner.

| Component | |
|---|---|
| 5-[2-(Dimethylamino)ethyl]amino-5,11-dihydro[1]benzoxepino[3,4-b]pyridine trihydrochloride/hemihydrate (trihydrochloride/hemihydrate of compound 5) | 20 mg |
| Lactose | 280 mg |

EXAMPLE 40

Preparation of powder

A powder comprising the following components is prepared in a conventional manner.

| Component | |
|---|---|
| 5,11-Dihydro-5-[(N,N—diisopropylamino)-acetyl]amino[1]benzoxepino[3,4-b]- | 25 mg |

| Component | |
|---|---|
| pyridine (compound 27) | |
| Lactose | 275 mg |

EXAMPLE 41

Preparation of syrup

A syrup comprising the following components is prepared in a conventional manner.

| Component | |
|---|---|
| 5-[2-(Diisopropylamino)ethyl]amino-5,11-dihydro[1]benzoxepino[3,4-b]pyridine trihydrochloride/hemihydrate (trihydrochloride/hemihydrate of compound 24) | 300 mg |
| Sucrose | 40 g |
| Methyl para-hydroxybenzoate | 40 mg |
| Propyl para-hydroxybenzoate | 10 mg |
| Strawberry flavour | 0.1 cc |

Water is added to the above components until the total volume is 100 cc.

EXAMPLE 42

Preparation of syrup

A procedure similar to that in Example 41 was employed except that 5-[(N,N-diethylamino)acetyl]amino5,11-dihydro[1]benzoxepino[3,4-b]pyridine monofumarate/1.5-hydrate (monofumarate/1.5-hydrate of compound 28) was used instead of trihydrochloride/hemihydrate of compound 24.

What is claimed is:

1. A novel [1]benzepino[3,4-b]pyridine derivative represented by the formula (I):

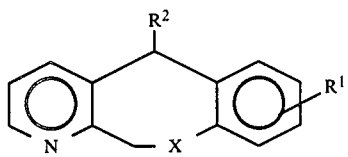

wherein $R^1$ represents a hydrogen atom, an alkyl group, a halogenated alkyl group, an alkoxy group or a halogen atom; $R^2$ represents

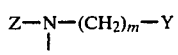

wherein Y represents an amino group, a substituted amino group, a heterocyclic group or a substituted heterocyclic group; Z represents a hydrogen atom, an alkyl group or an acyl group; and m is an integer of 1-3,

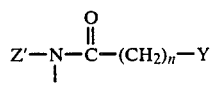

wherein Z' represents a hydrogen atom or an alkyl group; Y has the same meaning as defined above, and n is 0, 1 or 2; or

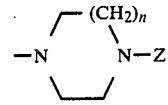

wherein Z and n have the same meanings as defined above; X represents an oxygen atom or a sulfur atom; and the pharmaceutically acceptable acid addition salts thereof.

2. A derivative of claim 1; namely, 5-[2-(diethylamino)ethyl]amino-5,11-dihydro[1]benzoxepino[3,4-b]pyridine.

3. A derivative of claim 1; namely, 5-[2-(dimethylamino)ethyl]amino-5,11-dihydro[1]benzoxepino[3,4-b]pyridine.

4. A derivative of claim 1; namely, 5-[3-(diethylamino)propyl]amino-5,11-dihydro[1]benzoxepino[3,4-b]pyridine.

5. A derivative of claim 1; namely, 5-[2-(1-pyrrolidinyl)ethyl]amino-5,11-dihydro[1]benzoxepino[3,4-b]pyridine.

6. A derivative of claim 1; namely, 5-[2-(morpholino)ethyl]amino-5,11-dihydro[1]benzoxepino[3,4-b]pyridine.

7. A derivative of claim 1; namely, 5-[1-(4-methyl)-piperazinyl]-5,11-dihydro[1]benzoxepino[3,4-b]pyridine.

8. A derivative of claim 1; namely, 5-[2-(diisopropylamino)ethyl]amino-5,11-dihydro[1]benzoxepino[3,4-b]pyridine.

9. A derivative of claim 1; namely, 5,11-dihydro-5-[(N,N-diisopropylamino)acetyl]amino[1]benzoxepino[3,4-b]pyridine.

10. A derivative of claim 1; namely, 5-[(N,N-diethylamino)acetyl]amino-5,11-dihydro[1]benzoxepino[3,4-b]pyridine.

11. A derivative of claim 1; namely, 5,11-dihydro-5-[(4-methyl-1-piperazinyl)acetyl]amino[1]benzoxepino[3,4-b]pyridine.

12. A derivative of claim 1; namely, 1-(5,11-dihydro[1]benzoxepino[3,4-b]pyridin-5-yl)1,3-dimethylurea.

13. A derivative of claim 1; namely, 1-(5,11-dihydro[1]benzoxepino[3,4-b]pyridin-5-yl)1,3-diethylurea.

14. A pharmaceutical composition comprising a pharmaceutical carrier and, as an active ingredient, an effective amount of a novel [1]benzepino[3,4-b]pyridine derivative represented by formula (I)

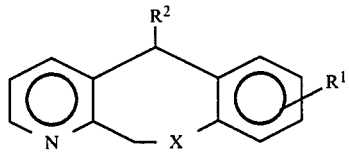

wherein $R^1$ represents a hydrogen atom, an alkyl group, a halogenated alkyl group, an alkoxy group or a halogen atom; $R^2$ represents

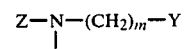

wherein Y represents an amino group, a substituted amino group, a heterocyclic group or a substituted heterocyclic group; Z represents a hydrogen atom, an alkyl group or an acyl group; and m is an integer of 1-3,

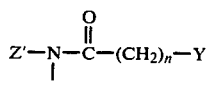

wherein Z' represents a hydrogen atom or an alkyl group; Y has the same meaning as defined above, and n is 0, 1 or 2; or

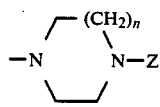

wherein Z and n have the same meanings as defined above; X represents an oxygen atom or a sulfur atom; and the pharmaceutically acceptable acid addition salts thereof.

15. A pharmaceutical composition according to claim 14, wherein the derivative is 5-[2-(diethylamino)ethyl]amino-5,11-dihydro[1]benzoxepino[3,4-b]pyridine.

16. A pharmaceutical composition according to claim 14, wherein the derivative is 5-[2-(dimethylamino)ethyl]amino-5,11-dihydro[1]benzoxepino[3,4-b]pyridine.

17. A pharmaceutical composition according to claim 14, wherein the derivative is 5-[3-(diethylamino)propyl]amino-5,11-dihydro[1]benzoxepino[3,4-b]pyridine.

18. A pharmaceutical composition according to claim 14, wherein the derivative is 5-[2-(1-pyrrolidinyl)ethyl]amino-5,11-dihydro[19 benzoxepino[3,4-b]pyridine.

19. A pharmaceutical composition according to claim 14, wherein the derivative is 5-[2-(morpholino)ethyl]amino-5,11-dihydro[1]benzoxepino[3,4-b]pyridine.

20. A pharmaceutical composition according to claim 14, wherein the derivative is 5-[1-(4-methyl)-piperazinyl]5,11-dihydro[1]benzoxepino[3,4-b]pyridine.

21. A pharmaceutical composition according to claim 14, wherein the derivative is 5-[2-(diisopropylamino)ethyl]amino-5,11-dihydro[1]benzoxepino[3,4-b]pyridine.

22. A pharmaceutical composition according to claim 14, wherein the derivative is 5,11-dihydro-5-[(N,N-diisopropylamino)acetyl]amino[1]benzoxepino[3,4-b]pyridine.

23. A pharmaceutical composition according to claim 14, wherein the derivative is 5-[(N,N-diethylamino)acetyl]amino-5,11-dihydro[1]benzoxepino[3,4-b]pyridine.

24. A pharmaceutical composition according to claim 14, wherein the derivative is 5,11-dihydro-5-[(4-methyl-1-piperazinyl)acetyl]amino[1]benzoxepino[3,4-b]pyridine.

25. A pharmaceutical composition according to claim 14, wherein the derivative is 1-(5,11-dihydro[1]benzoxepino[3,4-b]pyridin-5-yl)1,3-dimethylurea.

26. A pharmaceutical composition according to claim 14, wherein the derivative is 1-(5,11-dihydro[1]benzoxepino[3,4-b]pyridin-5-yl)-1,3-diethylurea.

* * * * *